United States Patent
Zhao et al.

(10) Patent No.: US 12,024,494 B2
(45) Date of Patent: Jul. 2, 2024

(54) SALT OF LSD1 INHIBITOR AND A POLYMORPH THEREOF

(71) Applicant: CSPC ZHONGQI PHARMACEUTICAL TECHNOLOGY (SHIJIAZHUANG) CO., LTD., Hebei (CN)

(72) Inventors: Lele Zhao, Shanghai (CN); Jianjun Sun, Shanghai (CN); Lingyun Wu, Shanghai (CN); Shuhui Chen, Shanghai (CN)

(73) Assignee: CSPC ZHONGQI PHARMACEUTICAL TECHNOLOGY (SHIJIAZHUANG) CO., LTD., Hebei (CN)

( * ) Notice: Subject to any disclaimer, the term of this patent is extended or adjusted under 35 U.S.C. 154(b) by 737 days.

(21) Appl. No.: 17/261,322

(22) PCT Filed: Jul. 19, 2019

(86) PCT No.: PCT/CN2019/096842
§ 371 (c)(1),
(2) Date: Jan. 19, 2021

(87) PCT Pub. No.: WO2020/015745
PCT Pub. Date: Jan. 23, 2020

(65) Prior Publication Data
US 2021/0317096 A1 Oct. 14, 2021

(30) Foreign Application Priority Data
Jul. 20, 2018 (CN) .......................... 201810804068.3

(51) Int. Cl.
*C07D 271/06* (2006.01)
*A61P 35/00* (2006.01)

(52) U.S. Cl.
CPC ............ *C07D 271/06* (2013.01); *A61P 35/00* (2018.01); *C07B 2200/13* (2013.01)

(58) Field of Classification Search
None
See application file for complete search history.

(56) References Cited

U.S. PATENT DOCUMENTS 9,149,447 B2 10/2015 Muñoz et al.
9,795,597 B2 10/2017 Johnson et al.
(Continued)

FOREIGN PATENT DOCUMENTS

CN 102947265 A 2/2013
CN 103857393 A 6/2014
(Continued)

OTHER PUBLICATIONS

Berge SM, Bighley LD, Monkhouse DC. Pharmaceutical salts. J Pharm Sci. Jan. 1977;66(1):1-19. doi: 10.1002/jps.2600660104. PMID: 833720. (Year: 1977).*
(Continued)

*Primary Examiner* — Jeffrey S Lundgren
*Assistant Examiner* — Anthony Joseph Seitz
(74) *Attorney, Agent, or Firm* — Carter, DeLuca & Farrell LLP (57) ABSTRACT

Provided are a compound III serving as an LSD1 inhibitor and a crystal form thereof, as well as use of the compound and the crystal form thereof in preparation of a medicament for treating an LSD1 related disease.

(Continued)

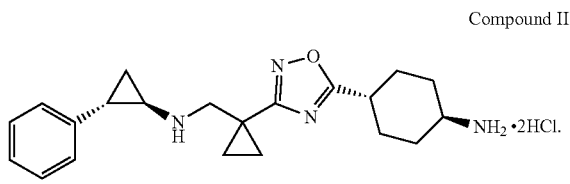

Compound III

7 Claims, 4 Drawing Sheets

(56) References Cited

U.S. PATENT DOCUMENTS

| 11,433,053 | B2* | 9/2022 | Wu | C07D 263/56 |
|---|---|---|---|---|
| 2020/0345700 | A1 | 11/2020 | Wu et al. | |

FOREIGN PATENT DOCUMENTS

| WO | 2010084160 A1 | 7/2010 |
|---|---|---|
| WO | 2012013728 A1 | 2/2012 |
| WO | 2017/184934 A1 | 10/2017 |
| WO | 2017/195216 A1 | 11/2017 |
| WO | 2018/137644 A1 | 8/2018 |

OTHER PUBLICATIONS

Extended European Search Report issued in corresponding EP Application No. 19837636.0, dated Feb. 18, 2022, pp. 1-8.
International Search Report issued in corresponding International Application No. PCT/CN2019/096842, dated Oct. 22, 2019, pp. 1-3, English Translation.

* cited by examiner

SALT OF LSD1 INHIBITOR AND A POLYMORPH THEREOF

CROSS REFERENCE TO RELATED APPLICATIONS

The present application is a national stage application of International Application No. PCT/CN2019/096842, filed Jul. 19, 2019, which claims the benefit and priority of Chinese Patent Application No. CN201810804068.3, filed Jul. 20, 2018, the entire contents of each of which are hereby incorporated by reference herein in their entirety.

TECHNICAL FIELD

The present disclosure relates to a compound III as an LSD1 inhibitor and its crystal form, and use of the compound and its crystal form in preparation of a medicament for treating an LSD1 related disease.

BACKGROUND ART

Epigenetics regulates gene expression through different mechanisms, including covalent modifications to histones, such as methylation or demethylation; covalent modifications to DNA, such as methylation or hydroxymethylation; and reorganization of nuclear chromatin. Although these modifications do not change the basic sequence of DNA, such epigenetic change may persist throughout the cell life cycle or cell iteration process through cell division [Adrian Bird, Nature, 2007, 396-398]. Therefore, epigenetic dysfunction may cause and participate in pathological process of various diseases, such as various solid tumors, hematomas, viral infections, neurological abnormalities and other diseases. Therefore, epigenetics has now become a research hotspot in the field of drug development. Lysine-specific demethylase (LSD1, also called KDM1A) as the first demethylase discovered in 2004, belongs to the family of flavin adenine dinucleotide (FAD)-dependent amino oxidases. The structure of LSD1 consists of three major domains: an N-terminal SWIRM domain, a C-terminal amino oxidase domain (AOL) and a central protruding Tower domain. The C-terminal amino oxidase domain includes two active pockets, one is the site for binding to FDA, and the other is the site for recognizing and binding to a substrate. There is no clear conclusion about the function of the SWIRM domain. It does not directly participate in the binding of FAD or substrates, but mutation or removal of this region will reduce the activity of LSD1. Therefore, it is speculated that this region may affect active region by adjusting its conformation. The tower domain is the domain where LSD1 binds to other protein factors. LSD1 binds to different protein factors and acts on different substrates, thereby exerting different regulatory effects on histone and gene expression. For example, after combined with CoREST, LSD1 will preferentially act on histone H3K4, remove activation-related histone markers by demethylation, and thus inhibit gene transcription; and after combined with androgen receptor protein, the recombined LSD1 will preferentially act on H3K9, and activate androgen receptor-related gene transcription through demethylation. In addition, LSD1 has some non-histone receptors, such as p53, E2F1, DNMT1, MYPT1.

LSD1 is an FAD-dependent amino oxidase, in which proton transfer is considered as the most likely oxidation mechanism. First, the N—$CH_3$ bond of the substrate is converted into an imine bond through proton transfer. This imine ion intermediate undergoes a hydrolysis reaction to generate a demethylated amine and a formaldehyde. During this catalytic cycle, FAD is reduced to $FADH_2$, which is then oxidized back to FAD by a molecule of oxygen, while generating a molecule of $H_2O_2$.

LSD1 is an indispensable regulator in epigenetics. It modifies histones through demethylation and is therefore called as the "eraser" enzyme in the organism. LSD1 can regulate gene expression, thereby regulating cell proliferation and differentiation.

SUMMARY OF THE INVENTION

The present disclosure provides a compound III:

Compound III

The present disclosure also provides a crystal form A of the compound III, having an X-ray powder diffraction (XRPD) pattern with characteristic diffraction peaks at 2θ angles of: 4.72±0.2°, 14.24±0.2° and 21.78±0.2°.

In some aspects of the present disclosure, the X-ray powder diffraction pattern of the above crystal form A has characteristic diffraction peaks at 2θ angles of: 4.72±0.2°, 14.24±0.2°, 16.28±0.2°, 17.14±0.2°, 20.72±0.2°, 21.78±0.2°, 23.98±0.2° and 24.96±0.2°.

In some aspects of the present disclosure, the X-ray powder diffraction pattern of the above crystal form A has characteristic diffraction peaks at 2θ angles of: 4.72±0.2°, 14.24±0.2°, 16.28±0.2°, 17.14±0.2°, 17.58±0.2°, 18.70±0.2°, 20.72±0.2°, 21.78±0.2°, 23.98±0.2°, 24.96±0.2° and 26.22±0.2°.

In some aspects of the present disclosure, the X-ray powder diffraction pattern of the above crystal form A has characteristic diffraction peaks at 2θ angles of: 4.721°, 9.479°, 14.242°, 16.279°, 17.141°, 17.581°, 18.082°, 18.702°, 20.719°, 21.780°, 22.278°, 23.978°, 24.959°, 26.22°, 26.779°, 27.358°, 27.978°, 28.656°, 29.244°, 30.738°, 32.699°, 33.159°, 33.940°, 35.201° and 37.637°.

Figure 1:
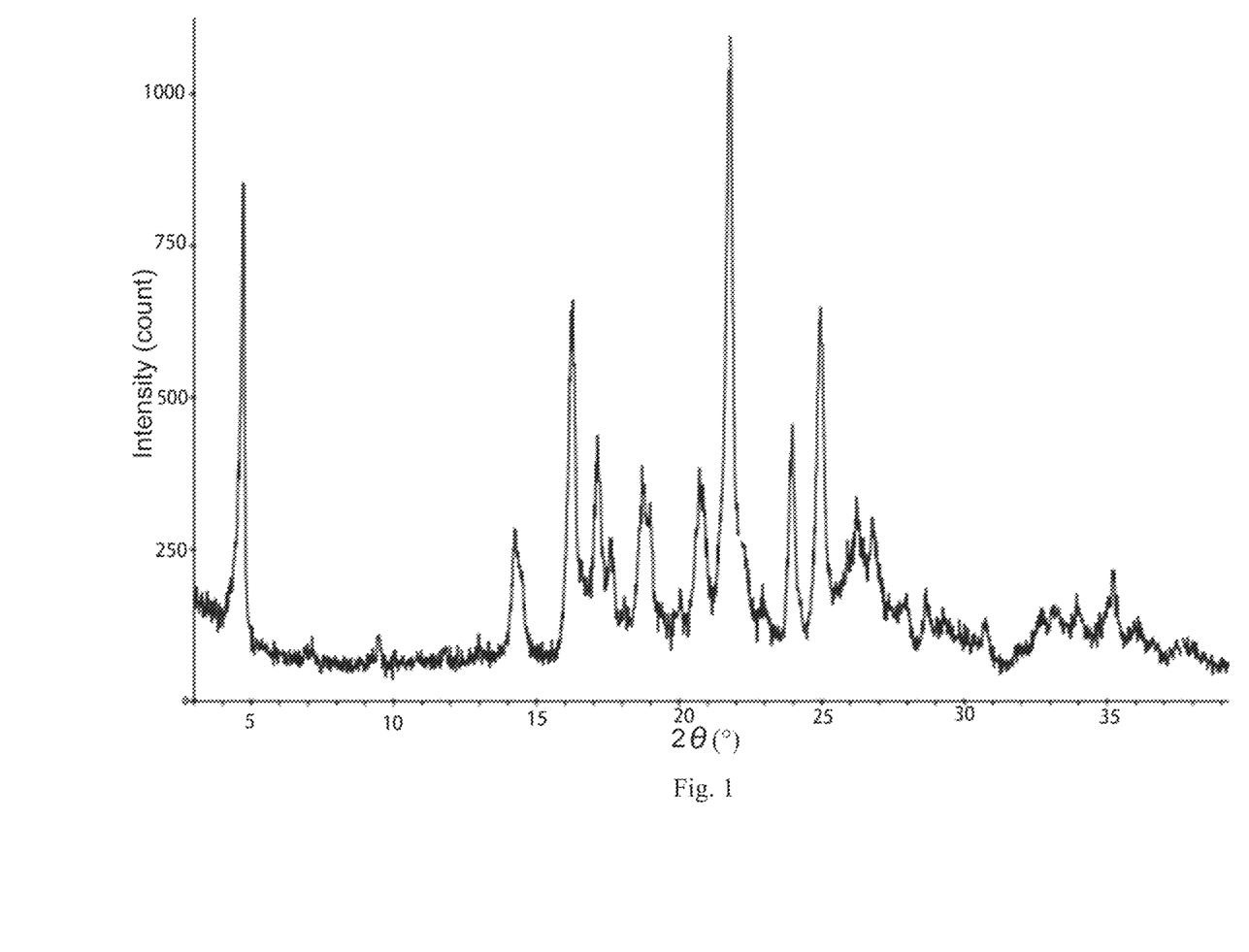
FIG. 1 is the XRPD pattern by Cu—Kα radiation of crystal form A of compound III.

In some aspects of the present disclosure, the XRPD pattern of the above crystal form A is substantially as shown in FIG. 1.

In some aspects of the present disclosure, the XRPD pattern analysis data of the above crystal form A is shown in Table 1:

TABLE 1

XRPD pattern analysis data of crystal form A

| No. | 2θ (°) | Interplanar spacing (Angstrom) | Background | Intensity | Relative Intensity (%) | area | area % | Half width |
|---|---|---|---|---|---|---|---|---|
| 1 | 4.721 | 18.7027 | 77 | 776 | 82.6 | 11380 | 67.8 | 0.249 |
| 2 | 9.479 | 9.3229 | 62 | 46 | 4.9 | 418 | 2.5 | 0.155 |
| 3 | 14.242 | 6.2139 | 75 | 208 | 22.2 | 4345 | 25.9 | 0.355 |
| 4 | 16.279 | 5.4406 | 73 | 587 | 62.4 | 12072 | 72 | 0.35 |
| 5 | 17.141 | 5.1688 | 73 | 364 | 38.7 | 7120 | 42.4 | 0.333 |
| 6 | 17.581 | 5.0405 | 73 | 196 | 20.8 | 6533 | 38.9 | 0.567 |
| 7 | 18.082 | 4.9018 | 73 | 99 | 10.5 | 1030 | 6.1 | 0.177 |
| 8 | 18.702 | 4.7408 | 137 | 249 | 26.5 | 5177 | 30.9 | 0.353 |
| 9 | 20.719 | 4.2836 | 153 | 231 | 24.5 | 3782 | 22.5 | 0.279 |
| 10 | 21.78 | 4.0773 | 155 | 940 | 100 | 16777 | 100 | 0.304 |
| 11 | 22.278 | 3.9873 | 115 | 143 | 15.2 | 7131 | 42.5 | 0.846 |
| 12 | 23.978 | 3.7082 | 121 | 334 | 35.6 | 4100 | 24.4 | 0.209 |
| 13 | 24.959 | 3.5647 | 153 | 495 | 52.7 | 7533 | 44.9 | 0.259 |
| 14 | 26.22 | 3.3961 | 168 | 169 | 18 | 4286 | 25.5 | 0.432 |
| 15 | 26.779 | 3.3264 | 173 | 130 | 13.8 | 2327 | 13.9 | 0.305 |
| 16 | 27.358 | 3.2573 | 92 | 71 | 7.6 | 2553 | 15.2 | 0.61 |
| 17 | 27.978 | 3.1865 | 92 | 85 | 9.1 | 1421 | 8.5 | 0.284 |
| 18 | 28.656 | 3.1126 | 96 | 89 | 9.5 | 1567 | 9.3 | 0.299 |
| 19 | 29.244 | 3.0514 | 91 | 62 | 6.6 | 2223 | 13.3 | 0.613 |
| 20 | 30.738 | 2.9064 | 58 | 79 | 8.4 | 1769 | 10.5 | 0.381 |
| 21 | 32.699 | 2.7364 | 70 | 83 | 8.9 | 4417 | 26.3 | 0.902 |
| 22 | 33.159 | 2.6995 | 70 | 88 | 9.4 | 4082 | 24.3 | 0.786 |
| 23 | 33.94 | 2.6392 | 70 | 106 | 11.3 | 2576 | 15.4 | 0.412 |
| 24 | 35.201 | 2.5474 | 104 | 111 | 11.8 | 1810 | 10.8 | 0.278 |
| 25 | 37.637 | 2.388 | 68 | 35 | 3.7 | 1058 | 6.3 | 0.514 |

In some aspects of the present disclosure, the differential scanning calorimetry (DSC) curve of the above crystal form A has an onset of the exothermic peak at 194.66±3° C.

Figure 2:
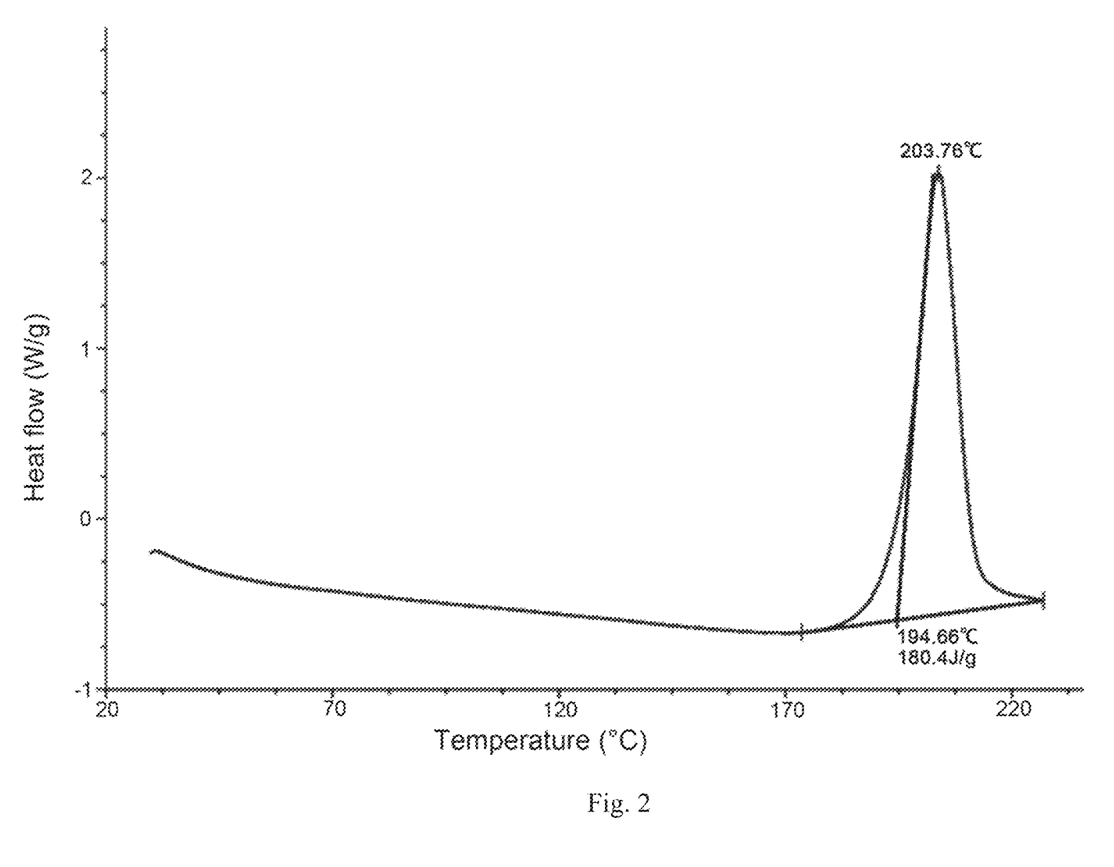
FIG. 2 is the DSC pattern of crystal form A of compound III.

In some aspects of the present disclosure, the DSC pattern of the above crystal form A is substantially as shown in FIG. 2.

In some aspects of the present disclosure, the thermogravimetric analysis (TGA) curve of the above crystal form A has a weight loss of 1.331% at 194.21±3° C.

Figure 3:
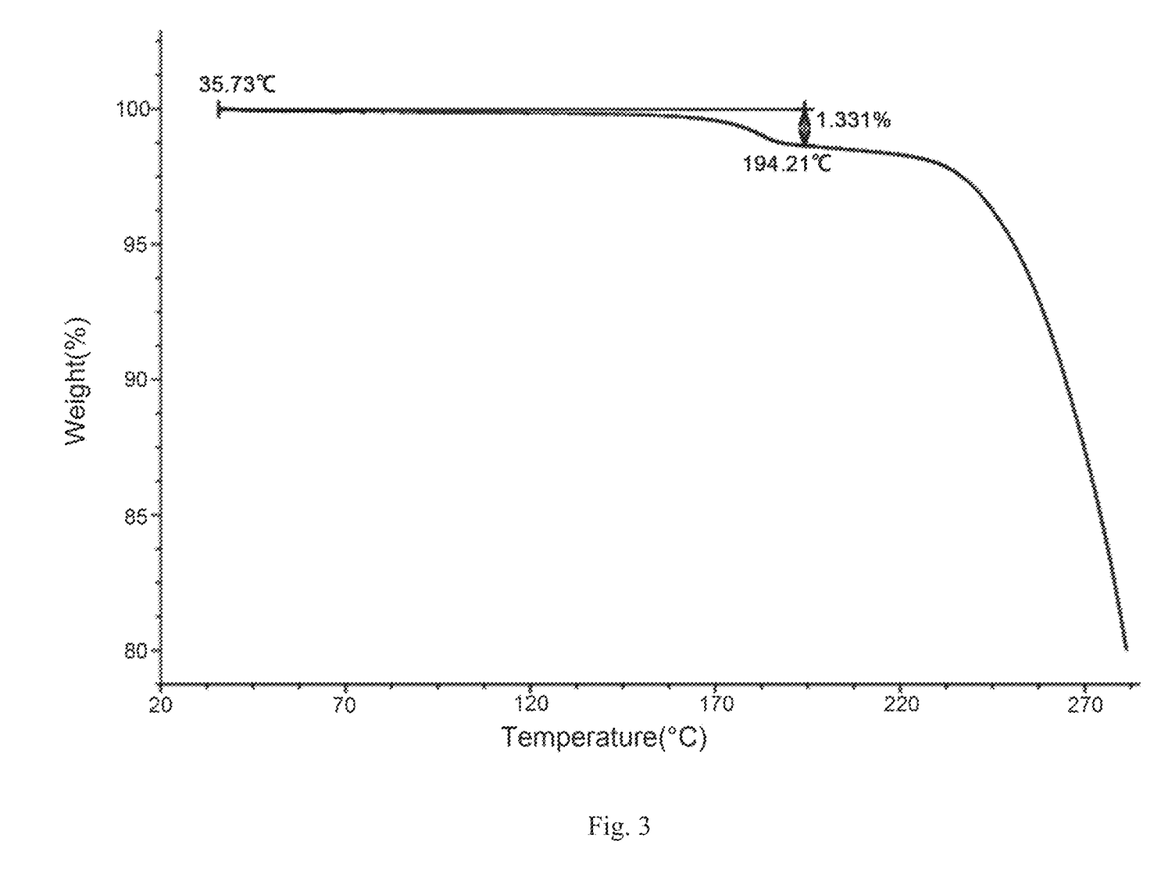
FIG. 3 is the TGA pattern of crystal form A of compound III.

In some aspects of the present disclosure, the TGA pattern of the above crystal form A is substantially as shown in FIG. 3.

The present disclosure also provides the use of the above compound III or the above crystal form A in preparation of a medicament for treating an LSD1 related disease.

The present disclosure also provides the use of the above compound III or the above crystal form A in preparation of a medicament for treating lung cancer, especially small cell lung cancer.

Technical Effect

The compound III and its crystal form A of the present disclosure have good LSD1 inhibitory activity and superior in vivo effects; and as compared to the free base thereof and other salts, they have good stability and excellent solubility, and are less affected by light, heat and humidity, and thus have a promising prospect for becoming a medicine.

Definition and Description

Unless otherwise stated, the following terms and phrases used herein are intended to have the following meanings. A specific phrase or term should not be considered uncertain or unclear without a special definition, but should be understood in its ordinary meaning. When a trade name appears herein, it is intended to refer to its corresponding commodity or its active ingredient.

The intermediates of the present disclosure can be prepared by a variety of synthetic methods well known to those skilled in the art, including the specific embodiments listed below, the embodiments formed by combining them with other chemical synthesis methods, and the equivalent alternative embodiments well-known by those skilled in the arts, preferred embodiments include but are not limited to the examples of the present disclosure.

The chemical reaction in the specific embodiment of the present disclosure is completed in a suitable solvent, and the solvent must be suitable for the chemical change of the present disclosure and the required reagents and materials. In order to obtain the compounds of the present disclosure, it is sometimes necessary for those skilled in the art to modify or select the synthesis steps or reaction schemes based on the existing embodiments.

The present disclosure will be specifically described below through examples, and these examples are not intended to limit the present disclosure in any way.

All solvents used in the present disclosure are commercially available and can be used without further purification.

The solvents used in the present disclosure are commercially available. The present disclosure employs the following abbreviations: DCM represents dichloromethane; DMF represents N,N-dimethylformamide; DMSO represents dimethyl sulfoxide; EtOH represents ethanol; MeOH represents methanol; TFA represents trifluoroacetic acid; TsOH represents p-toluenesulfonic acid; mp represents melting point; $EtSO_3H$ represents ethanesulfonic acid; $MeSO_3H$ represents methanesulfonic acid; ATP represents adenosine triphosphate; HEPES represents 4-hydroxyethylpiperazine ethanesulfonic acid; EGTA represents ethylene glycol bis(2-aminoethylether)tetraacetic acid; $MgCl_2$ represents magnesium dichloride; $MnCl_2$ represents manganese dichloride; DTT represents dithiothreitol; DCC represents dicyclohexylcarbodiimide; DMAP represents 4-dimethylaminopyridine.

X-Ray Powder Diffraction (by X-Ray Powder Diffractometer, XRPD) Method of the Present Disclosure Instrument model: DX-2700BH X-ray diffractometer
Test method: approximately 10 to 20 mg of sample is used for XRPD detection.
The detailed XRPD parameters are as follows:
Ray source: Cu, k-Alpha1 (λ=1.54184 Å)
Light tube voltage: 40 kV, light tube current: 30 mA
Divergence Slit: 1 mm
The first Soller Slit: 28 mm, the second Soller Slit: 28 mm
Receiving Slit: 0.3 mm, anti-scatter slit: 1 mm
Measuring time: 0.5 s
Scanning angle range: 3-40 deg
Step width angle: 0.02 deg
The Differential Scanning Calorimeter (DSC) Analytic Method of the Present Disclosure
Instrument model: TA Q2000 Differential Scanning Calorimeter
Test method: a sample (about 1 mg) was taken and placed in a DSC aluminum pan for testing. The sample was heated from 30° C. (room temperature) to 300° C. (or 350° C.) at a heating rate of 10° C./min under 50 mL/min of $N_2$.
The Thermal Gravimetric Analyzer (TGA) Analytic Method of the Present Disclosure
Instrument model: TA Q5000 thermogravimetric analyzer
Test method: a sample (2 to 5 mg) was taken and placed in a TGA platinum pan for testing. The sample was heated from room temperature to 300° C. or to a weight loss of 20% at a heating rate of 10° C./min under 25 mL/min of $N_2$.
The Dynamic Vapor Adsorption (DVS) Analytic Method of the Present Disclosure
Instrument model: SMS DVS Advantage dynamic vapor adsorption instrument Test conditions: a sample (10~15 mg) was taken and placed in the DVS sample pan for testing.
The detailed DVS parameters are as follows:
Temperature: 25° C.
Balance: dm/dt=0.01%/min (shortest: 10 min, longest: 180 min)
drying: drying at 0% RH for 120 min
RH (%) test step: 10%
RH (%) test step range: 0%-90%-0%
The Classification of Hygroscopicity Evaluation is as Follows:

| Classification of hygroscopicity | ΔW % |
| --- | --- |
| Deliquescence | Absorb enough water to form a liquid |
| Very hygroscopic | ΔW % ≥ 15% |
| Hygroscopic | 15% > ΔW % ≥ 2% |
| Slightly hygroscopic | 2% > ΔW % ≥ 0.2% |
| No/little hygroscopicity | ΔW % < 0.2% |

Note:
ΔW % represents the moisture gain of the test product at 25 ± 1° C. and 80 ± 2% RH.

DETAILED EMBODIMENTS

In order to better understand the content of the present disclosure, a further description is given below in combination with specific examples, but the specific embodiments are not intended to limit the content of the present disclosure.

Example 1: Preparation of Compound I

Synthetic Scheme:

Sodium hydroxide (279 g, 6.99 mol) was dissolved in water (3.00 L), maintained at about 10° C., and added with the compound A (997 g, 3.49 mol) in batches. After the solid was completely dissolved, the mixture was extracted by ethyl acetate (2.00 L×2). The combined organic phase was washed with water (1.50 L) and saturated brine (1.50 L) successively, dried over anhydrous sodium sulfate, and filtered. The filtrate was concentrated under reduced pressure to give the compound I. $^1$H NMR (400 MHz, CDCl$_3$) δ 7.18-7.14 (m, 2H), 7.07-7.05 (m, 1H), 6.94-6.92 (m, 2H), 2.47-2.44 (m, 1H), 1.78-1.76 (m, 1H), 0.97-0.94 (m, 1H), 0.92-0.89 (m, 1H).

Example 2: Preparation of Compound II

Synthetic Scheme:

Step I

The compound 1 (260 g, 1.87 mol) was dissolved in tetrahydrofuran (2.00 L) and methanol (200 mL), maintained at about 20° C., and added with sodium borohydride (70.8 g, 1.87 mol) in batches. The reaction mixture was stirred at 20° C. for 18 hours, added dropwise with a saturated sodium bicarbonate solution (2.00 L) at 0° C. to quench the reaction until no bubbles were generated. A small amount of solid was formed. The reaction mixture was filtered. The solid residue was washed with ethyl acetate (1.00 L×2). The filtrate was added with solid sodium chloride to supersaturation and layered. The organic phase was washed with a saturated brine (1.00 L). The combined aqueous phase was extracted with a mixed solution of ethyl acetate and tetrahydrofuran (ethyl acetate:tetrahydrofuran=10:1, 1.00 L×3). The combined organic phase was washed with a saturated brine (1.00 L), dried over anhydrous sodium sulfate, filtered, and concentrated under reduced pressure to give the compound 2. $^1$H NMR (400 MHz, CDCl$_3$) δ 3.63 (s, 2H), 2.20 (s, 1H), 1.29 (dd, J$_1$=5.2 Hz, J$_2$=2.0 Hz, 2H), 0.99 (dd, J$_1$=5.2 Hz, J$_2$=2.0 Hz, 2H).

Step II

The compound 2 (101 g, 1.04 mol) was dissolved in anhydrous dichloromethane (1.50 L), maintained at 5° C. to 10° C., and added with Dess-martin periodinane (486 g, 1.14 mol) in batches. The reaction mixture was stirred at 25° C. for 12 hours, and then controlled below 15° C., and slowly added with a saturated aqueous sodium bicarbonate (4.00 L), followed by slow addition of a saturated sodium thiosulfate solution (4.00 L). After stirred for 30 minutes, the reaction mixture was stood to be layered. The aqueous phase was extracted with dichloromethane (1.00 L×3), and the combined organic phase was washed with water (1.00 L×1) and saturated brine (1.00 L×1) in sequence, dried over anhydrous sodium sulfate, filtered, and concentrated under reduced pressure to obtain the compound 3. $^1$H NMR (400 MHz, CDCl$_3$) δ 9.31 (s, 1H), 1.71-1.68 (m, 4H).

Step III

The compound I (97.5 g, 732 mmol) and the compound 3 (83.5 g, 878 mmol) were dissolved in dry dichloromethane (1.50 L) and added with acetic acid (4.40 g, 73.2 mmol). The reaction mixture was stirred at 26° C. for 4 hours, added with sodium triacetoxyborohydride (232 g, 1.10 mol), and stirred at 25° C. for 12 hours. After slowly addition of a saturated sodium bicarbonate solution (3.50 L) until no bubbles were generated, the reaction mixture was stood to be layered. The aqueous phase was extracted with dichloromethane (1.00 L×1), and the combined organic phase was concentrated under reduced pressure to remove the organic solvent. The residue was added with water (800 mL), adjusted pH to 3 with an aqueous hydrochloric acid (1 M) and extracted with tert-butyl methyl ether (800 mL×2). The aqueous phase was adjusted pH with saturated sodium bicarbonate to 8 and extracted with dichloromethane (1.00 L×2). The combined organic phase was dried over anhydrous sodium sulfate, and concentrated under reduced pressure to give the compound 4. $^1$H NMR (400 MHz, CDCl$_3$) δ 7.29-7.26 (m, 2H), 7.19-7.16 (m, 1H), 7.06-7.04 (m, 2H), 2.83 (s, 2H), 2.51-2.48 (m, 1H), 2.01-1.96 (m, 1H), 1.28-1.24 (m, 2H), 1.18-1.13 (m, 1H), 1.05-1.01 (m, 1H), 0.88-0.79 (m, 2H). MS-ESI calculated: [M+H]$^+$ 213, found: 213.

Step IV

The compound 4 (113 g, 534 mmol) was dissolved in tetrahydrofuran (1.20 L) and water (300 mL), added with di-tert-butyl dicarbonate (128 g, 588 mmol) and lithium hydroxide monohydrate (26.9 g, 641 mmol). The reaction mixture was stirred at 25° C. for 12 hours, adjusted pH with aqueous hydrochloric acid (1 M) to 3, and extracted with ethyl acetate (800 mL×2). The organic phase was washed with saturated brine (1.00 L×1), dried with anhydrous sodium sulfate, and concentrated under reduced pressure. The residue was added with n-heptane (1.00 L), stirred for 12 hours to generate a large amount of white solid, and filtered. The filter cake was dried under reduced pressure to obtain the compound II. $^1$H NMR (400 MHz, CDCl$_3$) δ 7.23-7.21 (m, 2H), 7.13-7.10 (m, 1H), 7.07-7.05 (m, 2H), 3.42-3.31 (m, 2H), 2.90-2.88 (m, 1H), 2.10-2.05 (m, 1H), 1.37 (s, 9H), 1.28-1.16 (m, 4H), 1.00-0.90 (m, 2H). MS-ESI calculated: [M+H]$^+$ 313, found: 313.

Example 3: Preparation of Compound III and its Crystal Form A

Synthetic Scheme:

II

Compound III

Step I

The compound II (202 g, 647 mmol) was dissolved in absolute ethanol (500 mL) at room temperature, added with diisopropylethylamine (209 g, 1.62 mol) and hydroxylamine hydrochloride (90.0 g, 1.30 mol), heated to 80° C. and stirred for 16 hours. The reaction solution was cooled to room temperature, and concentrated under reduced pressure to remove ethanol. The residue was dissolved in ethyl acetate (2.00 L). The organic phase was washed with water (500 mL×3), dried over anhydrous sodium sulfate, and filtered. The filtrate was concentrated. The residue was dissolved in ethyl acetate (200 mL), added with n-heptane (2.00 L) under stirring, and further stirred for 12 hours to precipitate a white solid. The resultant was filtered, and the filter cake was washed with n-heptane (200 mL), and dried at 45° C. under vacuum for 12 hours to obtain the compound 5. $^1$H NMR (400 MHz, DMSO-d6) δ 8.92 (s, 1H), 7.27-7.23 (m, 2H), 7.16-7.08 (m, 3H), 5.26 (s, 2H), 3.53-3.50 (m, 1H), 3.32-3.28 (m, 1H), 2.78-2.76 (m, 1H), 2.03-2.00 (m, 1H), 1.33 (s, 9H), 1.14-1.11 (m, 2H), 0.71-0.59 (m, 4H). MS-ESI calculated: $[M+H]^+$ 346, found: 346.

Step II

The compound 6 (126 g, 532 mmol) was dissolved in anhydrous N,N-dimethylformamide (1.40 L), added with carbonyldiimidazole (88.8 g, 557 mmol) at 30° C. under nitrogen protection and stirred for 3 hours. The reaction mixture was added with the compound 5 (175 g, 506 mmol), heated to 110° C. and stirred for 12 hours. The reaction solution was cooled to room temperature, slowly added to water (14 L) under stirring to precipitate a lot of white solid, and filtered. The filter cake was washed with water (3 L×3) and dried at 30° C. under vacuum to give the compound 7. $^1$H NMR (400 MHz, CDCl$_3$) δ 7.28-7.23 (m, 2H), 7.17-7.14 (m, 1H), 7.06-7.05 (m, 2H), 4.43-4.41 (m, 1H), 3.88-3.70 (m, 2H), 3.48-3.47 (m, 1H), 2.76-2.73 (m, 2H), 2.14-2.07 (m, 5H), 1.64-1.61 (m, 2H), 1.46 (s, 9H), 1.41 (s, 9H), 1.24-1.00 (m, 7H). MS-ESI calculated: $[M+Na]^+$ 575, found: 575.

Step III

The compound 7 (240 g, 434 mmol) was dissolved in ethyl acetate (240 mL), added with a solution of hydrochloric acid in ethyl acetate (4M, 820 mL) under stirring at 0° C., stirred at 0° C. to 25° C. for 3 hours to precipitate a lot of white solid, and filtered. The filter cake was washed with ethyl acetate (500 mL×5), and dried at 40° C. under vacuum to give the compound III. The compound III was added to absolute ethanol (1.20 L), heated to reflux under stirring until all the solids were dissolved, and filtered hot to remove mechanical impurities. A small amount of solids were precipitated in the filtrate. The refluxing was continued so that all the solids were dissolved and the stirring was stopped. The filtrate was cooled at a rate of 10° C. to 20° C. per 1 to 2 hours. After cooled to 45° C., the filtrate was maintained for 12 hours to precipitate a lot of white solid. Then the filtrate was cooled at a rate of 10° C. to 20° C. per 1 to 2 hours again until the temperature was 25° C., stirred evenly and filtered. The filter cake was washed with isopropanol (260 mL×3), and dried under vacuum at 45° C. After detected by XRPD, the crystal form A of the compound III was obtained. $^1$H NMR (400 MHz, CD$_3$OD) δ 7.32-7.29 (m, 2H), 7.25-7.21 (m, 1H), 7.17-7.14 (m, 2H), 3.70-3.62 (m, 2H), 3.21-3.14 (m, 1H), 3.09-3.05 (m, 1H), 3.01-2.95 (m, 1H), 2.57-2.52 (m, 1H), 2.26-2.22 (m, 2H), 2.18-2.15 (m, 2H), 1.75-1.64 (m, 2H), 1.61-1.54 (m, 3H), 1.44-1.41 (m, 2H), 1.39-1.36 (m, 1H), 1.34-1.32 (m, 2H). MS-ESI calculated: $[M+H]^+$ 353, found: 353.

Example 4: Test of Chloride Ion Content in the Crystal Form A of the Compound III Experimental instrument: Ion chromatography ICS5000
Chromatographic Parameters:
Guard column: Dionex IonPac AG11-HC, 4×50 mm Guard column
Chromatographic column: Dionex IonPac AS11-HC, 4×250 mm Guard column
Column temperature: 30° C.
Detection mode: conductivity detection
Flow rate: 1.0 mL/min
ASRS-4 mm suppressor 18 mA
Injection volume: 25 μL
Analysis time: 20 min
Mobile phase: 7 mM KOH
Sample Preparation:
Three samples of 50 mg crystal form A of Compound III were weighed accurately and labeled as Sample 1, Sample 2 and Sample 3. They were dissolved with deionized water and brought to volume to prepare three solutions of 0.2 mg/mL.
Experimental Results:

TABLE 2

Test result of chloride ion content in the crystal form A of the compound III
Content of Chloride ion (%)

| Calculated Value | Measured Value (averages value of 3 measurement) | error |
| --- | --- | --- |
| 16.7 | 17.0 | 0.3 |

Experimental Conclusions:

The measured value of chloride ion content in the crystal form A of the compound III is consistent with the theoretical value thereof with an error of less than 0.3%, and this product is a dihydrochloride.

Example 5: Study of Hygroscopicity of the Crystal Form A of the Compound III Experimental Materials: SMS DVS Advantage dynamic vapor adsorption instrument Experimental Methods 10 to 15 mg of the crystal form A of the compound III was taken and placed in a DVS sample pan for testing.

Figure 4:
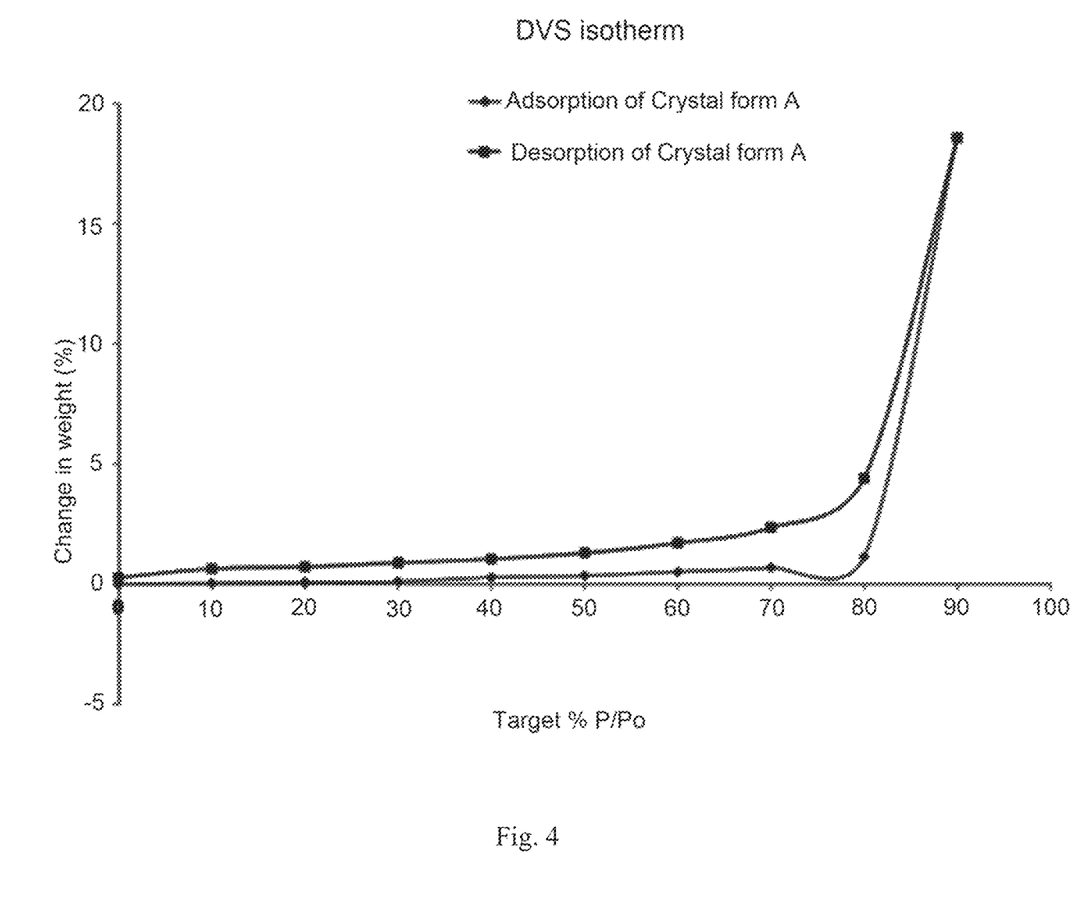
FIG. 4 is the DVS isotherm of crystal form A of compound III.

Experimental Results:

The DVS spectrum of the crystal form A of the compound III is shown in FIG. 4 with ΔW=1.14%.

Experimental Conclusion:

The crystal form A of the compound III has a moisture weight gain of 1.14% at 25° C. and 80% RH, exhibiting slightly hygroscopic.

Example 6: Test of Solid Stability of the Crystal Form A of the Compound III

According to the "Guiding Principles for Testing of Stability of API and Preparations" (Chinese Pharmacopoeia 2015, Edition Four, General Principles 9001), the stability of the crystal form A of the compound III was investigated under conditions of high temperature (60° C., open), high humidity (room temperature/relative humidity 92.5%, open) and light (total illuminance=1.2×10$^6$ Lux·hr/near-UV=200 W·hr/m$^2$, open).

10 mg of the crystal form A of the compound III was weighed, placed in the bottom of a glass vial, and spread into a thin layer. For the samples placed under the conditions of high temperature (60° C.) and high humidity (relative humidity of 92.5% RH), the bottle opening was sealed with an aluminum foil, and some small holes were pierced in the aluminum foil to ensure that the sample can be sufficiently in contact with ambient air, and the samples were placed in the corresponding constant temperature and humidity ovens. The sample exposed to light (open, not covered with aluminum foil) and the control sample (the entire sample bottle was covered with aluminum foil) were placed in a light box. At each time point, 2 samples were weighed as formal test samples. Another 50 mg of the crystal form A of the compound III was weighed for XRPD testing. The sample bottles were wrapped with an aluminum foil, and the aluminum foil was pierced with small holes. They were also placed in the corresponding constant temperature and humidity ovens. The sample was taken and detected (by XRPD) at the 5th day and 10th day, and the detection results were compared with the initial detection result at 0 day. The test results are as shown in the following table 3:

TABLE 3

Test result of solid stability of the crystal form A of the compound III

| Test conditions | Time point | Crystal form |
| --- | --- | --- |
| — | 0 day | Crystal Form A |
| High temperature | 5$^{th}$ day | Crystal Form A |
| (60° C., open) | 10$^{th}$ day | Crystal Form A |
| High humidity | 5$^{th}$ day | Crystal Form A |
| (relative humidity 92.5%, open) | 10$^{th}$ day | Crystal Form A |
| Light (total illuminance = 1.2 × 10$^6$ | 5$^{th}$ day | Crystal Form A |
| Lux · hr/near ultraviolet = 200 w · hr/m$^2$, open) | 10$^{th}$ day | Crystal Form A |

Conclusion: The crystal form A of the compound III has good stability under the conditions of high temperature, high humidity and strong light.

Example 7: Test of Solvent Stability of the Crystal Form A of the Compound III

Appropriate amounts of the compound III were weighed and added to different glass vials, and added respectively with appropriate amount of a solvent or a solvent mixture to prepare a suspension. After added with a magnet rotor and placed at room temperature, the above samples were placed on a constant temperature mixer (40° C.) to be shaken for 2 days (avoid from light). In order to ensure that the sample was as suspended as possible, the amount of the compound and the solvent would be adjusted according to the test phenomenon and even the container used in the experiment may be changed during the experiment. (The dissolved sample was evaporated naturally to dryness). The test results were shown in the following Table 4:

TABLE 4

Test result of solvent stability of the crystal form A of the compound III

| No. | Solvent | Weight (mg) | Solvent volume (μL) | Status | Crystal form |
| --- | --- | --- | --- | --- | --- |
| 1 | Acetonitrile | 32 | 300 + 200 | Suspending | Crystal form A |
| 2 | Tetrahydrofuran | 31 | 200 + 200 | Suspending | Crystal form A |
| 3 | Isopropyl acetate | 30 | 200 + 400 | Suspending | Crystal form A |
| 4 | Isopropanol | 31 | 200 + 200 | Suspending | Crystal form A |
| 5 | Methanol | 20 | 100 | Dissolved, and then Precipitated | Crystal form A |

Conclusion: The crystal form A of the compound III has good stability in the solvent.

Experimental Example 1: Study of LSD1 Inhibition of the Crystal Form A of the Compound III 1.1 Experimental Purpose:

The experimental purpose was to evaluate $IC_{50}$ of the crystal form A of the compound III at 10 concentrations against LSD1. The experiment was conducted in duplicate with an initial concentration of 10 μM diluted in a gradient of 3 times, and it was repeated twice at different dates.

1.2 Test Conditions:

LSD1 buffer composition: 50 mM Tris-HCl, pH 7.5, 0.05% CHAPS, 1% DMSO.

Reaction time: reacted at room temperature for 1 hour

Reaction Process:

1.2.1 Adding enzyme to a freshly prepared buffer 1.2.2 Adding a DMSO solution of the compound to the enzyme mixture using Acoustic Technology (Echo 550, LabCyte Inc. Sunnyvale, CA) at nL level, and incubating at room temperature for 30 minutes 1.2.3 Adding the substrate to a freshly prepared buffer 1.2.4 Incubating at room temperature for 1 hour 1.2.5 Preparing to test the mixture 1.2.6 Using Perkin Elmer Envision to read data 1.2.7 Using Excel and GraphPad Prism software to analyze data 1.3 Test Results:

TABLE 5

LSD1 Inhibition of the crystal form A of the compound III

| Compound | $IC_{50}$ (nM) Mean ± standard deviation |
| --- | --- |
| Crystal form A of Compound III | 8.0 ± 0.6 |

Conclusion: This experiment evaluated LSD1 inhibition of the crystal form A of the compound III with the enzyme fluorescent conjugated method. The results showed that the crystal form A of compound III has a significant inhibitory effect against LSD1 with $IC_{50}$=8 nM.

Experimental Example 2: In Vivo Efficacy Study of the Crystal Form A of the Compound III on Human Small Cell Lung Cancer NCI-H1417 Cell Subcutaneous Xenograft Tumor in CB-17 SCID Mouse Model 2.1 Experimental Purpose:

The experimental purpose is to evaluate the in vivo efficacy of the crystal form A of the compound III of the present disclosure on human small cell lung cancer NCI-H1417 cell subcutaneous xenograft in a CB-17 SCID mouse model.

2.2 Experimental Animals:

Species: Mouse

Strain: CB-17 SCID mouse

Week age and weight: 6-8 weeks old, weight: 16-21 grams

Sex: female

Supplier: Shanghai Lingchang Biological Technology Co., Ltd.

2.3 Experimental Method and Procedures 2.3.1 Cell Culture

Human small cell lung cancer NCI-H1417 cells were cultured in a monolayer in vitro with RPMI-1640 medium plus 10% fetal bovine serum, at 37° C. and 5% $CO_2$ to culture and passage. When the cell saturation was 80%-90%, the cells were collected by trypsin-EDTA digestion, counted, adjusted to $10 \times 10^7$ cells/mL and resuspended in PBS.

2.3.2 Tumor Cell Inoculation 0.2 mL ($10 \times 10^6$ cells) of NCI-H1417 cells (with Matrigel, volume ratio 1:1) were subcutaneously inoculated on the right back of each mouse. When the average tumor volume reached about 100-150 mm³, the mice were grouped randomly and started to be administered.

2.3.3 Preparation of Test Substance

The experimental vehicle was a 0.5% methyl cellulose solution. 5 g of methyl cellulose was weighed, dissolved in 800 mL of ultrapure water, stirred evenly and brought to the volume of 1000 mL with ultrapure water. The test substance was dissolved in the vehicle, prepared into a uniform solution of a certain concentration, and stored at 4° C.

2.3.4 Tumor Measurement and Experimental Indicator

The experimental indicator was to investigate whether the tumor growth was inhibited, delayed or cured. The tumor diameter was measured with a vernier caliper twice a week. The tumor volume is calculated by the formula of $V = 0.5 a \times b^2$, where a and b represent the long diameter and short diameter of the tumor, respectively.

TGI (%) is used for the anti-tumor efficacy of the compound. TGI (%) reflects the tumor growth inhibition rate. TGI (%)=[(1−(Average tumor volume at the end of the administration of a certain treatment group−average tumor volume at the beginning of the administration of the treatment group))/(Average tumor volume at the end of treatment in the vehicle control group−Average tumor volume at the beginning of the treatment in the vehicle control group)]× 100%. Vehicle control group: Vehicle (0.5% methylcellulose solution).

TABLE 6

Evaluation of anti-tumor efficacy of the crystal form A of the compound III on human small cell lung cancer NCI-H1417 xenograft tumor model (Calculated based on tumor volume on day 35 after administration)

| Group | Tumor volume (mm³) (Day 35) | TGI (%) (Day 35) |
| --- | --- | --- |
| Vehicle | 443 ± 41 | — |
| Crystal form A of Compound III (1 mg/kg, PO, QD) | 178 ± 17 | 81.9 |
| Crystal form A of Compound III (1.5 mg/kg, PO, QD) | 121 ± 15 | 99.2 |
| Crystal form A of Compound III (3 mg/kg, PO, QD) | 68 ± 13 | 115.6 |

Conclusion: The crystal form A of the compound III of the present disclosure has an excellent anti-tumor effect on the human small cell lung cancer NCI-H1417 xenograft tumor model.

The invention claimed is:

1. A crystal form A of compound III, wherein the X-ray powder diffraction pattern has characteristic diffraction peaks at 2θ angles of: 4.72±0.2°, 14.24±0.2°, 16.28±0.2°, 17.14±0.2°, 20.72±0.2°, 21.78±0.2°, 23.98±0.2° and 24.96±0.2°, Compound III 2. The crystal form A according to claim 1, wherein the X-ray powder diffraction pattern has characteristic diffraction peaks at 2θ angles of: 4.72±0.2°, 14.24±0.2°, 16.28±0.2°, 17.14±0.2°, 17.58±0.2°, 18.70±0.2°, 20.72±0.2°, 21.78±0.2°, 23.98±0.2°, 24.96±0.2° and 26.22±0.2°.

3. The crystal form A according to claim 2, wherein the X-ray powder diffraction pattern has characteristic diffraction peaks at 2θ angles of: 4.721°, 9.479°, 14.242°, 16.279°, 17.141°, 17.581°, 18.082°, 18.702°, 20.719°, 21.780°, 22.278°, 23.978°, 24.959°, 26.22°, 26.779°, 27.358°, 27.978°, 28.656°, 29.244°, 30.738°, 32.699°, 33.159°, 33.940°, 35.201° and 37.637°.

4. The crystal form A according to claim 1, further comprising a differential scanning calorimetry (DSC) curve with an onset of the exothermic peak at 194.66±3° C.

5. The crystal form A according to claim 1, further comprising a thermogravimetric analysis (TGA) curve with a weight loss of 1.331% at 194.21=3° C.

6. A method for treating lung cancer, comprising administering to a subject in need of such treatment an effective amount of the crystal form A according to claim 1.

7. The method according to claim 6, wherein the lung cancer is small cell lung cancer.

* * * * *